United States Patent [19]

Tosoni

[11] Patent Number: 4,490,470
[45] Date of Patent: Dec. 25, 1984

[54] PROCESS FOR THE SEPARATION AND PURIFICATION OF DEXTRANASE

[75] Inventor: Anthony L. Tosoni, Willowdale, Canada

[73] Assignee: Polydex Chemicals Ltd., Nassau, The Bahamas

[21] Appl. No.: 455,235

[22] Filed: Jan. 3, 1983

[51] Int. Cl.³ .............................................. C12N 9/46
[52] U.S. Cl. ..................................... 435/211; 435/816
[58] Field of Search ................................. 435/211, 816

[56] References Cited

U.S. PATENT DOCUMENTS 3,047,471  7/1962  Hurst et al. ...................... 435/816 X
3,477,910  11/1969  Sloane ............................. 435/816 X
3,652,401  3/1972  Chaiet et al. .................... 435/816 X
3,702,805  11/1972  Ishibashi et al. ................ 435/816 X

OTHER PUBLICATIONS

Chemical Abstracts vol. 72, 2172t, (1970).

Primary Examiner—Lionel M. Shapiro
Attorney, Agent, or Firm—I. Louis Wolk

[57] ABSTRACT

This invention relates to a novel process for the separation, purification and recovery of dextranase from impure solutions such as fermentation broth by precipitating a complex of dextranase with tannic acid and thereafter separating the purified dextranase from the tannic acid.

6 Claims, No Drawings

PROCESS FOR THE SEPARATION AND PURIFICATION OF DEXTRANASE

BACKGROUND OF THE INVENTION

Dextranase is an enzyme which is derived from the cultivation of various enzyme producing organisms by fermentation of nutrient containing media comprising dextran. Such organisms include strains of fungi such as P. Funiculosum, P. Lilacinum, Chaetomium gracile and others, as well as various strans of bacilli.

Various procedures for the recovery and separation of dextranase are also well know as by salting out, precipitation with acetone, absorption on clay of DEAE cellulose, chromatography and iso-electric precipitation.

Processes for the preparation and recovery of dextranase are described in the prior art, as for example, U.S. Pat. Nos. 3,663,371, 3,787,289, 3,912,594, 3,627,643, and others.

Previous methods for the separation and purification of dextranase involve problems of cost and complexity particularly where high strength and purity are desired.

DESCRIPTION OF THE INVENTION

Applicant has now discovered that dextranase can be precipitated from solutions or broths obtained by fermentation of dextran solutions with suitable organisms by means of tannic acid. The precipitate is in the form of a complex of tannic acid and dextranase from which dextranase can be separated in a concentrated and purified state.

In carrying out the process, broth from fermentation, containing dextranase, is preferably clarified by centrifuging or other means and is then mixed with a suitable quantity of tannic acid. The pH of the solution is adjusted, in most cases to 3-3.5 with HCl and mixed by gentle stirring for a period of time determined experimentally for a given broth. Generally a period of ½-1 hour is sufficient.

After mixing is complete, the tannic acid and dextranase have formed a complex which precipitates and settles. The clear supernatant liquid is drawn off and the precipitate is further isolated by centrifuging or otherwise. The isolated complex is in the form of a gel composed of tannic acid, dextranase and water along with other impurities.

The separated precipitate is washed with acetone by dispersing it in a comparatively large volume of acetone which dissolves the tannic acid and leaves the solid partially purified dextranase behind. The solid is then separated, preferably by centrifuging. For a higher degree of purity, the acetone wash can be repeated once or twice of more if necessary. The residue is air-dried. Further purification may be accomplished by extracting dextranase with water or aqueous buffers. The aqueous extracts, after treatment with charcoal to remove colour, if desired, may be freeze-dried to give a friable powder.

Other solvents for tannic acid such as ethanol may be used to dissolve the tannic acid from the complex, without dissolving the enzyme.

The tannic acid may be added to the broth in powder form although an aqueous solution of 5-20% is ordinarily used.

The following examples illustrate the manner in which the invention has been carried out.

EXAMPLE I

A broth was obtained by fermentation in a stainless steel vessel of P. funiculosum in a medium containing dextran as described in the prior art. The broth had a potency of 17,300 dextranase units per ml.

After centrifuging and filtration, the clear 950 liters of broth (16.4 billion units of dextranase) were admixed with 150 liters of a 10% (w/v) aqueous solution of food-grade tannic acid with slow stirring. While stirring was continued, the pH was adjusted to 3-3.5 with hydrochloric acid. Gentle stirring was continued for one-half hour after which the resulting mixture was allowed to settle overnight. The clear supernatant liquid was drawn off and the remaining bottom slurry was centrifuged to remove most of the water. The weight of the retained brown gel was 2.0 kilos. Eighteen liters of cold acetone (4° C.) were added with stirring to disperse the gel and facilitate dissolving of the tannic acid. The resulting suspension was centrifuged to separate the solid which was then resuspended as above in 3 more liters of cold acetone. All acetone extractions were carried out in the cold (4° C.). After centrifuging there was obtained a solid which after air drying gave 281 grams of friable powder.

This powder was suspended in 2.8 liters of water and the mixture was stirred for 1½ hours. The mixture was then centrifuged yielding a first extract at 2.5 liters.

A second extract made by adding 1.4 liters was obtained. It measured 1.45 liters.

A third extract made by adding 1.4 liters of water, measured 1.4 liters.

The three extracts were combined. 40 grams of powdered Norit—Ex Charcoal was added, the mixture was stirred for 1½ hours and filtered. The charcoal was washed with small portions of water on the filter and the washings were added to the first filtrate to give 5800 ml which assayed at 1.78 million units per ml for a total of 10.3 billion units. The non-volatile residue for this solution was 19.5 mg per ml. The potency of the dissolved dextranase was therefore 91,300 $\mu$/mg. The yield is $((5800 \times 1,780,000) \div (950,000 \times 17,300)) \times 100 = 62.8\%$.

The solid enzyme may be isolated by well-known methods such as freeze-drying, precipitation with acetone, etc.

EXAMPLE II

A broth was obtained by fermentation of P. lilacinum $D_2$ in a medium containing dextran. After centrifuging to clarify, there was obtained 200 ml of clear broth which assayed 8900 $\mu$/ml. To it was added with slow stirring 30 ml of a 10% w/v aqueous solution of tannic acid. After stirring for 40 minutes the precipitate was separated by centrifuging in cups to yield a brown gel as in Example I. The gel was dispersed in 10 ml cold acetone and the acetone extract was separated by centrifuging. The acetone extraction was repeated three times. The extracted solids were air-dried and extracted with 10 ml of acetate buffer (pH 5.4). The extract assayed 119,000 $\mu$/ml. The yield is $((10 \times 119,000) \div (200 \times 8900)) \times 100 = 67\%$.

After taking into account, the non-volatile residue contributed by the acetate buffer the potency of the dissolved dextranase was calculated to be 11,500 $\mu$/mg.

EXAMPLE III

A broth was obtained by fermentation of Chaetomium gracile (ATCC 16153) in a medium containing dextran. After centrifuging to clarify there was obtained 116 ml of clear broth which assayed 14,760 $\mu$/ml. To it was added with slow stirring 18 ml of a 10% w/v aqueous solution of tannic acid. After stirring for 40 minutes the precipitate was separated by centrifuging and extracted with acetone as in Example II and the air-dried powder obtained was extracted with 10 ml of acetate buffer as in Example II.

The extract assayed 43,900 $\mu$/ml. The yield is $((10\times43,900)\div(116\times14,760))\times100=25.6\%$ After taking into account, the non-volatile residue contributed by the acetate buffer, the potency of the dissolved dextranase was calculated to be 12,400 $\mu$/mg.

The tannic acid may be used in varying degrees of purity ranging from laboratory grade, food grade or commercial grade, the choice depending upon economics and yield desired.

Units of dextranase activity as referred to herein are defined as "that amount of dextranase which in contact with dextran releases reducing sugar equivalent to 1.0 microgram of maltose monohydrate per minute at 37° C.".

1. A process for the recovery of purified dextranase from the broth containing products of fermentation of dextran which comprises clarifying such a fermentation solution to remove fermentation residues, contacting the resulting clarified solution with tannic acid in sufficient quantities to precipitate the dextranase in the form of a complex with tannic acid while maintaining the pH of the solution between 3 and 3.5, separating said complex, contacting the separated complex with a solvent for tannic acid to completely dissolve the tannic acid component of the complex, and recovering the dextranase as a dry residue.

2. A process according to claim 1 wherein the tannic acid is in the form of an aqueous solution which is admixed with the clarified broth with stirring, and wherein the tannic acid solvent is acetone.

3. A process according to claim 1 wherein the dry dextranase residue is extracted with water to dissolve dextranase from impurities in the residue and purified dextranase is recovered in dry form from said extract.

4. A process according to claim 3 wherein the dry residue is extracted a plurality of times with water and the aqueous extracts are combined prior to recovery of the dextranase in dry form.

5. A process according to claim 4 wherein the dried purified dextranase is recovered by air drying of the purified dextranase solution.

6. A process according to claim 4 wherein the dried purified dextranase is recovered by freeze drying of the purified dextranase solution.

* * * * *